(12) United States Patent
Nishida

(10) Patent No.: US 6,429,265 B2
(45) Date of Patent: *Aug. 6, 2002

(54) MOISTURE-ABSORBING AND DESORBING POLYMER AND COMPOSITIONS DERIVED THEREFROM

(75) Inventor: Ryosuke Nishida, Oku-gun (JP)

(73) Assignee: Japan Exlan Company Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/547,878

(22) Filed: Apr. 12, 2000

(30) Foreign Application Priority Data

Jun. 28, 1999 (JP) .............................. 11-181462

(51) Int. Cl.⁷ .............................. C08F 8/44; C08F 20/04; C08F 20/06
(52) U.S. Cl. .............................. 525/329.5; 525/327.4; 525/329.1; 525/329.4; 525/329.5; 525/329.7; 525/330.3; 525/366; 525/367; 526/317.1
(58) Field of Search ................................ 525/366, 367, 525/329.5, 329.7, 317.1, 330.3

(56) References Cited

U.S. PATENT DOCUMENTS

| 3,313,784 A | | 4/1967 | Vrancken et al. ........... 260/78.4 |
| 4,618,631 A | * | 10/1986 | Takeda ..................... 521/109.1 |
| 4,959,061 A | | 9/1990 | Cabestany ................... 604/368 |
| 4,985,514 A | | 1/1991 | Kimura et al. ................. 526/88 |
| 5,053,460 A | | 10/1991 | Mallo et al. .................. 525/116 |
| 5,055,501 A | | 10/1991 | Moriya et al. ............... 523/409 |
| 5,098,951 A | | 3/1992 | Mallo et al. .................. 525/116 |
| 5,292,822 A | | 3/1994 | Tanaka et al. ............. 525/329.1 |
| 5,473,023 A | | 12/1995 | Mizukami et al. ........ 525/329.2 |
| 6,080,797 A | * | 6/2000 | Nishida ........................ 521/64 |

FOREIGN PATENT DOCUMENTS

| EP | 0 882 502 | 12/1998 |
| FR | 1 514 673 | 5/1968 |
| JP | 5-105704 | 4/1993 |
| JP | 5-132858 | 5/1993 |
| JP | 8-225610 | 9/1996 |

* cited by examiner

Primary Examiner—Fred Zitomer
(74) Attorney, Agent, or Firm—Wenderoth, Lind & Ponack, L.L.P.

(57) ABSTRACT

Disclosed herein is a moisture-absorbing and desorbing polymer, characterized in that, the said polymer is an organic high-molecular substance containing 1.0-8.0 meq/g of carboxyl group of a potassium type and having a cross-linking structure.

6 Claims, No Drawings

MOISTURE-ABSORBING AND DESORBING POLYMER AND COMPOSITIONS DERIVED THEREFROM

1. BACKGROUND FIELD OF THE INVENTION

The present invention relates to a moisture-absorbing and desorbing polymer having high moisture-absorbing and desorbing properties and particularly having high moisture-absorbing and desorbing rates and also relates to compositions containing the same.

2. DESCRIPTION OF THE RELATED ART

With regard to a means for removing moisture in air, moisture absorbents such as lithium chloride, calcium chloride, magnesium chloride and phosphorus pentaoxide have been used. However, although such moisture absorbents have much moisture absorbing capacity and quick moisture absorbing rate, they are deliquescent and, therefore, there are disadvantages that they are liquefied after absorption of moisture and soil other substance, apt to be dissolved and difficult for their regeneration. Although other moisture absorbents such as silica gel, zeolite, sodium sulfate, active alumina and active carbon do not have such a problem, they have disadvantages that their moisture absorbing capacity is low, their moisture absorbing rate is slow, their regeneration require a high temperature and their repeated absorption and desorption of moisture result in pulverization which are causes that their practical use is disturbed.

On the other hand, with regard to moisture absorbents of an organic type, ultra water-absorbing resins represented by that of a polyacrylate type may be utilized as a moisture absorbent. However, in the case of such ultra water-absorbing resins, their water-absorbing property is very good but their moisture-absorbing property is not satisfactory. The specific problems are that their retention of water is so high that desorption of moisture hardly occurs, an equilibrium moisture absorption capacity at low humidity is low, they become tacky with absorption of moisture and their moisture absorbing rate is slow. With regard to the poor moisture desorption and problems at low temperature and of tackiness, solutions thereof have been attempted in the Japanese Laid-Open Patent Hei-05/132,858 by the proposal of highly moisture-absorbing and desorbing fiber consisting of organic polymer and in the Japanese Laid-Open Patent Hei-08/225,610 by the proposal of organic moisture-absorbing and desorbing fine particles. However, slow moisture-absorbing and desorbing rates have been still pointed out as a problem.

With regard to the moisture-absorbing rate, there is a proposal, for example, in the Japanese Laid-Open Patent Hei-05/105,704 for a method where polyacrylate and deliquescent inorganic salt are jointly used. It is mentioned there that, according to the said method, moisture-absorbing and desorbing properties at low humidity are improved whereby a product having a high moisture-absorbing property without dropping of water can be obtained. However, the time necessary for moisture absorption is in a level of hours (in the Examples, a significant increase in moisture absorption is noted during ten hours) and such a method is not satisfactory for the use requiring the moisture absorbing rate in the level of minutes or even seconds such as a rotary dehumidifier.

Such a moisture-absorbing rate is described in *Kogyo Zairyo,* volume 29, no. 8, page 18 where it is pointed out that highly hydrophilic polymers such as a high water-absorbing resin usually have slow moisture-absorbing rate. The reason therefor is mentioned that, because of an interaction among polar groups in the polymer, molecular movement of the polymer itself is suppressed whereby diffusion of water hardly takes place. It is also described that, with regard to a highly equilibrium moisture-absorbing amount at high humidity, the said interaction is gradually lost as the absorption of moisture proceeds whereby plasticization progresses and diffusion of water is apt to occur and, as a result, a relatively highly equilibrium moisture-absorbing amount is resulted at last.

PROBLEMS TO BE SOLVED BY THE INVENTION

An object of the present invention is to offer a polymer having high moisture-absorbing and desorbing properties and being able to express such moisture-absorbing and desorbing properties within a short period or, in other words, a polymer having moisture-absorbing and desorbing rates and also to offer compositions containing the said polymer. The present inventor has carried out an intensive study concentrating to moisture-absorbing and desorbing properties or, especially, moisture-absorbing and desorbing rates of moisture-absorbing and desorbing materials. As a result, he has found that the type of the salt of a carboxyl group greatly affects the moisture-absorbing and desorbing rates and has been able to prepare an organic polymer having high moisture-absorbing and desorbing properties and exhibiting excellent moisture-absorbing and desorbing rates which have not been available up to now whereupon the present invention has been accomplished.

SUMMARY OF THE INVENTION

The above-mentioned object of the present invention can be achieved by a moisture-absorbing and desorbing polymer which is characterized in that the said polymer is an organic high-molecular substance containing 1.0-8.0 meq/g of carboxyl group of a potassium salt type and having a cross-linking structure. Such a moisture-absorbing and desorbing polymer may be in any of the forms of fiber, particles and sheets and compositions containing the said polymer is useful where the rate of absorption and desorption of moisture is requested. As hereinafter, the present invention will be illustrated in detail.

DESCRIPTION OF THE PREFERRED EMBODIMENTS

First, it is necessary that the moisture-absorbing and desorbing polymer of the present invention contains 1.0–8.0 meq/g of carboxyl group of a potassium salt type and having a cross-linking structure. The highlight of the present invention and the key for achieving the excellent moisture-absorbing rate are that the carboxyl group is in a potassium salt type. Probably due to the fact that potassium is a commonly used alkaline metal, carboxyl group of a potassium type has been described by means of exemplification in the patents up to now including the known patents intended to give a high moisture-absorbing amount. However, that which has been described is merely exemplification and there has been no patent in which the relation between moisture-absorbing rate and the salt type of carboxyl group is specifically reported.

The present inventor has studied the relation between the moisture-absorbing and desorbing rates and the salt type of carboxyl group. In the literatures up to now, moisture-absorbing and desorbing properties at the equilibrium stage have been mostly discussed. Even in a few cases where moisture-absorbing and desorbing rates are discussed, the discussion is in a level of around ten minutes at the shortest and there has been no discussion in the level of one or two minutes or of seconds. The reason is due to the difficulty in a quantitative determination of the moisture-absorbing and desorbing rates of moisture-absorbing and desorbing materials. Thus, in the measurement of moisture-absorbing and desorbing rates of moisture-absorbing and desorbing material per se within a short period of time, the moisture-absorbing and desorbing rates are greatly affected by various factors such as form and shape of the moisture-absorbing and desorbing materials, measuring method, measuring conditions and measuring apparatus whereby a correct measurement is not possible. Against such a problem, the present inventor has succeeded in making a moisture-absorbing and desorbing material into a sheet on which the material is thinly and uniformly applied whereby it is subjected to a corrugate process to evaluate under a predetermined condition to overcome the problem whereupon a quantitative measurement of moisture-absorbing and desorbing rates within a short period of time has been made possible.

When the exchanging capacity of carboxyl group is same, the order of equilibrium moisture-absorbing amount per unit weight is sodium salt>potassium salt=lithium salt>rubidium salt>cesium salt but it has now been found that, in the case of treatment for two minutes or shorter, the order of moisture-absorbing rate in terms of quickness is potassium salt>rubidium salt>sodium salt=cesium salt>lithium salt. Accordingly, the conclusion is that, in order to obtain a quick moisture-absorbing rate, potassium salt is necessary as a salt type of carboxyl group.

The reason why moisture-absorbing rate of carboxyl group of a potassium type is quick has not been clearly clarified yet although, in "*Shin-Kagaku Library—Yoeki no Kagaku* (*New Chemistry Library—Chemistry of Solution*)" by Hitoshi Otaki, edited by the Chemical Society of Japan, there is a discussion on an alkaline metal ion in aqueous solution and movement of water molecules hydrated thereto. According to that, it is mentioned, in the case of lithium ion and sodium ion, movement of hydrated water molecule is slower than that in pure water and is bonded with the ion under "strong interaction" while, in the case of ions of potassium, rubidium and cesium, movement is rather mobile than that in pure water and, although water is bonded to ion, it is rather free as compared with pure water in terms of mobility. It is also mentioned there that, in rubidium and cesium ions, ionic radius is too big whereby the interaction of water molecule with ion becomes weak and the numbers of water molecules to be hydrated rather decrease.

On the other hand, it has been said that, in the case of porous substance such as silica gel and zeolite, its rate of adsorption of water is controlled by the diffusing rate in pores while the adsorbing rate of water into hydrophilic polymer is controlled by intramolecular diffusion. When the above fact and the mechanism for the phenomenon in water mentioned in the above literature are taken into consideration, it is presumed that, even in the system where water is integrated from atmospheric air (a hygroscopic system), the moving rate of moisturized water molecules is as quick as that in water and the amount of hydrated water is much in the case of carboxyl group of a potassium type whereby the best property in terms of the rate may be achieved.

The carboxyl group of a potassium type as such is a polar group having a high hydrophilicity for expressing a moisture-absorbing property and, in order to achieve a high moisture-absorbing property, it is preferred to contain the said group as many as possible. However, in order to make the moisture-absorbing rate quick together with the high moisture-absorbing amount, it is necessary that they are well-balanced in view of the ratio to the cross-linking structure. To be more specific, when amount of the said polar group is too much such as more than 8.0 meq/g, the ratio of the cross-linking structure which can be introduced is too small resulting in a product similar to a high water-absorbing resin. As a result, problems such as a stickiness is resulted as mentioned already or an extreme decrease in the rate is resulted whereby an object of the present invention cannot be achieved.

On the other hand, when amount of the said polar group is small, the moisture-absorbing and desorbing properties decrease and, especially when the amount is less than 1.0 meq/g, the resulting moisture-absorbing and desorbing properties are inferior to the above-mentioned moisture-absorbing inorganic materials whereby the practical value is lost. Practically, when amount of the said polar group is 4.0 meq/g or more or, more preferably, 6.0 meq/g or more, its priority as a moisture-absorbing and desorbing properties become significant as compared with the conventionally available other moisture-absorbing materials whereby favorable result is often available.

As a type of carboxyl group for achieving the object of the present invention, salt of a potassium type is essential as mentioned already and the best result is available when all carboxyl groups contained in the polymer are changed to potassium type. However, the coexistence of carboxyl groups where other alkaline metals such as Li, Na, Rb and Cs; alkaline earth metals such as Be, Mg, Ca, Sr and Ba; other metals such as Cu, Zn, Al, Mn, Ag, Fe, Co and Ni; $NH_4$; amine; or H as counter cations upon necessity is not out of scope of the present invention at all. In that case, there is no particular limitation for the ratio of potassium ion to other ions in the total carboxyl group but, in view of the moisture-absorbing and desorbing rates, the more the potassium ion, the better and, preferably, it is 40% or more or, more preferably, 60% or more.

Examples of a method for introduction of a carboxyl group by a chemical modification are that where a polymer consisting of a monomer being able to give a carboxyl group upon chemical modification is prepared and then hydrolysis is carried out to change to a carboxyl group. Examples of the monomer which can be used therefor are cyano-having monomer such as acrylonitrile and methacrylonitrile; and derivatives of acrylic acid, methacryllic acid, maleic acid, itaconic acid, vinylpropionyl acid, etc. such as esters [e.g., methyl (meth)acrylate, ethyl (meth)acrylate, n-propyl (meth)acrylate, isopropyl (meth)acrylate, n-butyl (meth) acrylate, n-octyl (meth)acrylate, 2-ethylhexyl (meth) acrylate and hydroxyethyl (meth)acrylate], anhydrides [e.g., maleic acid anhydride and itaconic acid anhydride] and amide compounds [e.g., (meth)acrylamide, dimethyl (meth) acrylamide, monoethyl (meth)acrylamide and n- or tert-butyl (meth)acrylamide].

With regard to other methods for introduction of carboxyl group by means of chemical modification, it is also possible to use a method where carboxyl group is introduced by oxidation reaction into a polymer having a double bond or a group which can be oxidized such as a halogen group, a hydroxyl group or an aldehyde group. For this oxidation reaction, the commonly used oxidization reaction may be applied and, after introduction of a carboxyl group, it is also possible to make into a potassium salt type by the same manner as mentioned above.

There is no particular limitation for other monomer which are copolymerizable with the above monomer and its examples are vinyl halide compounds such as vinyl chloride, vinyl bromide and vinyl fluoride; vinyliden monomer such as vinyliden chloride, vinyliden bromide and vinyliden fluoride; unsaturated carboxylic acid such as acrylic acid, methacrylic acid, maleic acid and itaconic acid and salts thereof; acrylates such as methyl acrylate, ethyl acrylate, butyl acrylate, octyl acrylate, methoxyethyl acrylate, phenyl acrylate and cyclohexyl acrylate; methacrylates such as methyl methacrylate, ethyl methacrylate, butyl methacrylate, octyl methacrylate, phenyl methacrylate and cyclohexyl methacrylate; unsaturated ketones such as methyl vinyl ketone, ethyl vinyl ketone, phenyl vinyl ketone, methyl isobutyl ketone and methyl isopropenyl ketone; vinyl esters such as vinyl formate, vinyl acetate, vinyl propionate, vinyl butyrate, vinyl benzoate, vinyl monochlroacetate, vinyl dichloroacetate, vinyl trichloroacetate, vinyl monofluoroacetate, vinyl difluoroacetate and vinyl trifluoroacetate; vinyl ethers such as methyl vinyl ether and ethyl vinyl ether; acrylamide and alkyl-substituted derivatives thereof; vinyl-containing acid compounds such as vinylsulfonic acid, allylsulfonic acid, methallylsulfonic acid, styrenesulfonic acid, 2-acrylamide-2-methylpropanesulfonic acid, sulfopropyl methacrylate, vinylstearic acid and vinylsulfinic acid and salts, anhydrides and derivatives thereof; styrene and alkyl- or halo-substituted derivatives such as styrene, methylstyrene and chlorostyrene; allyl alcohol or esters or ethers thereof; vinylimides such as N-vinylphthalimide and N-vinylsuccinoimide; basic vinyl compounds such as vinylpyridine, vinylimidazole, dimethylaminoethyl methacrylate, N-vinylpyrrolidone, N-vinylcarbazole and vinylpyridine; unsaturated aldehydes such as acrolein and methacrolein; and cross-linking vinyl compounds such as glycidyl methacrylate, N-methylolacrylamide, hydroxyethyl methacrylate, triallyl isocyanurate, triallyl cyanurate, divinylbenzene, ethylene glycol di(meth)acrylate, diethylene glycol di(meth)acrylate, triethylene glycol di(meth) acrylate, trimethylolpropane tri (meth) acrylate and methylenebisacrylamide.

There is no particular limitation for the cross-linking structure so far as it is not denatured physically or chemically as a result of moisture absorption and desorption but any structure such as cross-linking by covalent bond, ionic cross-linking and cross-linking by interpolymer interaction or crystalline structure will do. Further, there is no particular limitation for a method of introducing the cross-link and commonly used methods such as a cross-linking monomer at the stage of polymerization of main chain, post-cross-linking after polymerization and an introduction of cross-linking structure by physical energy may be used.

Among those, a method where a cross-linking monomer is used during the stage of polymerization of organic polymer to be used as a main chain and a method where a post-cross-linking is carried out after preparing a polymer are able to introduce a strong cross-linking structure by covalent bond.

In a method where a cross-linking monomer is used for example, it is possible to manufacture an organic polymer having a cross-linking structure due to covalent bond when the already-mentioned cross-linking vinyl compound is used and is copolymerized with a monomer which has carboxyl group or is able to change to carboxyl group. In that case however, in introducing an acrylic acid group, it is necessary to use a cross-linking monomer which is not chemically affected (such as hydrolysis) under an acidic condition (such as acrylic acid) or upon changing to carboxylic group whereby the applicable cross-linking monomers are limited.

Examples of the cross-link introduced by such methods are those introduced by cross-linking vinyl compounds such as glycidyl methacrylate, N-methylolacrylamide, triallyl isocyanurate, triallyl cyanurate, divinylbenzene, hydroxyethyl methacrylate, diethylene glycol di(meth)acrylate, triethylene glycol di(meth)acrylate, trimethylolpropane tri (meth)acrylate and methylenebisacrylamide. Among them, the cross-linking structure by triallyl isocyanurate, triallyl cyanurate, divinylbenzene and methylenebisacrylamide is chemically stable even, for example, at the stage of hydrolysis for introduction of carboxyl group and is preferred.

In addition, there is no particular limitation for a method by means of a post-cross-linking and its example is a post-cross-linking method where a hydrazine compound or formaldehyde is made to react with nitrile group in a nitrile compound wherein the content of vinyl monomer containing nitrile group is 50% by weight or more. In particular, a method using a hydrazine compound is quite good because it is possible to introduce a strong cross-link which is stable to acid and alkali, contributes to improvement in moisture-absorbing property due to the hydrophilicity of the cross-linking structure per se and is able to keep the form such as a porous form. Incidentally, with regard to the cross-linking structure obtained by the said reaction, its details have not been identified yet although it is presumed to be based upon a triazole ring or a tetrazole ring.

There is no particular limitation for the vinyl monomer having nitrile group so far as the monomer has nitrile group and its specific examples are acrylonitrile, methacrylonitrile, ethacrylonitrile, α-chloroacrylonitrile, α-fluoroacrylo-nitrile and vinylidene cyanate. Among them, acrylonitrile which is advantageous in view of the cost and has much amount of nitrile group per unit weight is most preferred.

There is no particular limitation for a method of introducing a cross-link by the reaction with a hydrazine compound so far as the aimed cross-linking structure is obtained and the method may be appropriately selected upon necessity such as concentrations of the acrylonitrile polymer and the hydrazine compound during the reaction, solvent used, reaction time and reaction temperature. With regard to reaction temperature among those, when it is too low, reaction rate becomes slow resulting in long reaction time while, when it is too high, plasticization of the starting acrylonitrile polymer takes place whereby the shape may be destroyed. Therefore, the preferred reaction temperature is 50-150° C. or, more preferably, it is 80–120° C. There is also no particular limitation for the part of the acrylonitrile polymer which is to be made to react with the hydrazine compound but the polymer may be appropriately selected depending upon the use and the shape of the said polymer. To be more specific, the reaction is carried out only on the surface of the polymer, the reaction is carried out into the core area throughout, the reaction is carried out by limiting to the specific area, etc. may be appropriately selected. Examples of the hydrazine compound used here are hydrazine hydrate; hydrazine salts such as hydrazine sulfate, hydrazine hydrochloride, hydrazine nitrate, hydrazine hydrobromide and hydrazine carbonate; and hydrazine derivative such as ethylenediamine, guanidine sulfate, guanidine hydrochloride, guanidine nitrate, guanidine phosphate and melamine.

Further, there is no particular limitation for a method of introducing a carboxyl group of a salt type by means of hydrolyzing reaction but known hydrolyzing conditions may be utilized. An example is a means where a basic aqueous solution such as alkaline metal hydroxide (particularly, potassium hydroxide) and ammonia, a mineral acid such as nitric acid, sulfuric acid or hydrochloric acid or an organic acid such as formic acid or acetic acid is added to the above-mentioned cross-linked acrylonitrile polymer followed by heating. With regard to the condition that the amount of carboxyl group of a potassium type in the present invention is 1.0–8.0 meq/g, it may be determined by means of experiments by clarifying the relation between the reaction factor (such as reaction temperature, concentration and time) and the amount of the carboxyl group of a potassium type to be introduced. Incidentally, it is also possible that the hydrolyzing reaction is carried out simultaneously with the above-mentioned introduction of cross-link. Here, when hydrolysis is carried out using a base except potassium hydroxide or using an acid, it is necessary that the carboxyl group is changed to that of a potassium salt type.

There is no particular limitation for the organic polymer in the present invention but known vinyl polymer may be used therefor. In carrying out the graft polymerization, there is no particular limitation for a polymer to be used as a stem but any of natural polymer, semi-synthetic polymer and synthetic polymer may be used. Specific examples of the polymer are plastic polymers such as polyethylene, polypropylene, vinyl chloride, ABS resin, Nylon, polyester, polyvinylidene chloride, polyamide, polystyrene, polyacetal, polycarbonate, acrylic resin, fluorine resin, polyurethane elastomer, polyester elastomer, melamine resin, urea resin, tetrafluoroethylene resin, unsaturated polyester resin, epoxy resin, urethane resin and phenol resin; common fiber-forming polymers such as Nylon, polyethylene, rayon, acetate, acrylate, polyvinyl alcohol, polypropylene, cupra, triacetate and vinylidene; natural rubber and polymer of synthetic rubber type such as silicone rubber, SBR (styrene-butadiene rubber), CR (chloroprene rubber), EPM (ethylene propylene rubber), FPM (fluorine rubber), NBR (nitrile rubber), CSM (chlorosulfonated polyethylene rubber), BR (butadiene rubber), IR (synthetic natural rubber), IIR (butyl rubber), urethane rubber and acrylic rubber.

There is no particular limitation for the shape of the moisture-absorbing and desorbing polymer per se in the present invention but any of particles, fiber and sheet may be appropriately selected. Among them, particles can be used as additives for various products in various uses and, therefore, they are useful because of wide applicable ranges. Size of the particle may be appropriately selected depending upon the use and there is no particular limitation. However, particles having an average particle size of 1000 $\mu$m or less or, more preferably, fine particles having an average particle size of 100 $\mu$m or less are of a big practical value because the applicable range as various additives becomes broad.

When the shape of the moisture-absorbing and desorbing polymer per se is fibrous, various processing to paper, nonwoven fabric, woven fabric, knitted product, processed fiber product, etc. can be easily conducted and the applicable use becomes wide whereby such a shape is useful. In the case of sheet, that is useful for the use as a filter which can be directly subjected to a processing such as corrugated paper.

When the moisture-absorbing and desorbing polymer of the present invention is made into a composition containing the same, its use spreads broadly. Especially when used as a processed product such as paper, nonwoven fabric, woven fabric, knitted product, sheet and foamed product, contacting area to gas is big and shape-holding property is good whereby it is useful as a material for moisture-absorbing and desorbing material. There is no particular limitation for the method for constituting them so far as the moisture-absorbing and desorbing polymer of the present invention is used and specific examples is that the form is constituted by the said polymer in a fibrous shape or the said polymer in particles is carried. However, in view of easy processing and low cost, good result is available when moisture-absorbing and desorbing polymer in particles is carried.

With regard to a method of carrying the moisture-absorbing and desorbing polymer of the present invention, it may be mixed with, impregnated into, applied to (using a binder) or contained in a matrix which constitutes the material and there is no particular limitation therefor but various methods may be adopted. The moisture-absorbing and desorbing polymer may be present in the said matrix or on the matrix surface. Thus, for example, a method where said polymer particles are mixed during the manufacturing stage of paper, nonwoven fabric, woven fabric, knitted thing, sheet, foamed product, etc., a method where a slurry of the said polymer particles is impregnated or applied using a binder and any other method may be adopted.

Specific examples are that, in the case of manufacture of paper from moisture-absorbing and desorbing polymer in particles or in fibrous form, the moisture-absorbing and desorbing polymer of the present invention in particles or in fibrous form is added to a slurry of materials for paper manufacture such as pulp or synthetic fiber dispersed in large amount of water followed, if necessary, by adding other necessary additives and the mixture is well mixed and made into paper using a common paper manufacturing machine. At that time, a fixing agent may be added, if necessary, for suppressing the loss of a filler by washing and examples of the fixing agent are modified polyethyleneimine, modified polyacrylamide, sodium alginate, gum arabic, soluble starch, aluminum sulfate and potassium alum. Amount of the fixing agent may be appropriately selected depending upon its type and the amount of the said polymer particles used. Further, sizing agent, dye, paper strength reinforcing agent, etc. which are commonly used in the manufacturing steps of paper may be appropriately used. With regard to a surface-active agent, that of anionic, cationic or nonionic type may be appropriately selected taking other additives into consideration and used. There is no particular limitation for the moisture-absorbing and desorbing polymer used for such a paper manufacture but, in the case of particles, favorable result is available when powder having a particle size of 1-100 $\mu$m is used. When the particle size is smaller than 1 $\mu$m, the powder falls down together with water from the net of the paper manufacturing machine while, when it is larger than 100 $\mu$m, the powder is too big whereby a problem that a homogeneous dispersing is difficult may happen. In the case of a fibrous shape, the finer the fiber diameter, the better but, practically, good result is available when it is 0.05-10 dtex and fiber length is 1-20 mm.

When used as a nonwoven fabric, there is no particular limitation but various methods may be used for adapting to nonwoven fabric. Specific examples in the case of a dry process are that of an adhesive type such as dipping method, printing method, spraying method, powder method and adhesive fiber method (thermal bond method), that of a mechanical bond type such as felt method, stitch method and needle punch method, that of a water flow entangling method such as spun lace method, and that of a spinning type such as spun bond method, network method, melt-blow method and film method while those in the case of a wet process are that of a water flow entangling type such as a spun race method, that of a spinning method such as spun bond method and flash spinning method, and that of a paper manufacturing type such as thermal fusion fiber method, thermal pressure method and adhesive method. There is also no particular limitation for a method for carrying the moisture-absorbing and desorbing polymer and, for example, in the case of fiber, fiber is mixed up with a fiber material constituting the nonwoven fabric whereby compositions can be easily prepared while, in the case of particles, various methods such as that they are sandwiched in those nonwoven fabric, that they are adhered with and carried on the fiber material constituting the nonwoven fabric and that they are applied on the surface of nonwoven fabric may be used for the carrying. Further, there is no particular limitation for weight per unit area although good result is often achieved when that is 20-300 g/m². When that is less than 10 g/m², strength is low resulting in breakage and the like while, when that is more than 300 g/m², there is a tendency of reduction in permeability of gas and liquid and that may be sometime unfavorable. Particularly favorable examples of the nonwoven fabric are a spun bond nonwoven fabric which is formed using a compounded fiber being comprised of a sheath part consisting of polyethylene and a core part consisting of polypropylene or polyester and a two-layered nonwoven fabric where the surface is a polyester fiber web layer while the back is a polypropylene web layer. Since those nonwoven fabrics can be easily processed due to the low-melting polyolefin component whereby it is possible to give a favorable material. When plastic foams are used for matrix, it is possible to prepare aimed plastic foams containing the said polymer by a common method where the said polymer particles are mixed with plastic foams such as foamed polyurethane or by a method where a slurry of moisture-absorbing and desorbing polymer particles is impregnated thereinto.

There is no particular limitation for the property of the polymer in the present invention but, when the polymer is made into a porous substance, further improvement in moisture-absorbing and desorbing rate can be achieved. To be more specific, a favorable result is available when there are macropores where the specific surface area is not less than 1 m²/g and an average pore diameter is 0.005-1.0 µm. There is a tendency that the more the specific surface area, the more the moisture-absorbing rate although it is not always true that, just when the specific surface area is big, the moisture-absorbing rate is fine. Thus, even when the specific surface area is big, there are some cases where pores per se disturb the diffusion of water molecules resulting in a reduction of moisture-absorbing rate if the average pore diameter is very small. Accordingly, with regard to the moisture-absorbing rate, it is important that the above-mentioned specific surface area and average pore diameter are well-balanced. The terms "specific surface area" used here stands for a value measured by means of a one-point method in a BET method which is a physical adsorption method. Another term "average pore diameter" stands for a value calculated by a formula (4V/S) where V is a pore volume per unit mass while S is a specific surface area obtained from a pore diameter distribution as measured by a mercury compression method.

EXAMPLES

The present invention will now be specifically illustrated by way of the following examples although the present invention is not limited to those examples. Unless otherwise mentioned, the terms "part(s)" and "%" used in the Examples are those by weight. First, method for evaluating the characteristics and the way of expressing the evaluated result will be illustrated.

Evaluation of moisture-absorbing property was carried out by means of an equilibrium moisture-absorbing ratio and a two-minute moisture-absorbing amount. The equilibrium moisture-absorbing ratio is the moisture-absorbing ratio obtained by the following method. Thus, about 1.0 g of moisture-absorbing material per se in particles or in fiber or a sheet sample is dried by a hot air drier at 105° C. for 16 hours to measure the weight (Wds) in grams, then the sample is allowed to stand for 24 hours in a chamber adjusted to and kept at the temperature of 20° C. and the relative humidity of 65% RH and the weight of the moistened sample is measured (Wws) in grams and, based upon the above result, calculation is made according to the following formula. Incidentally, in the case of a processed substance in a sheet, each of the weights is calculated using the weight of the moisture-absorbing and desorbing polymer per se after deducting the weight of the base material.

$$\text{Equilibrium moisture-absorbing ratio }(\%)=\{(Wws-Wds)/Wds\}\times 100$$

Method of measuring the two-minute moisture-absorbing amount is as follows. First, the sample for the measurement is prepared as follows. A sheet or paper having a thickness of about 200 µm containing 50 g/m² of a moisture-absorbing material is prepared. With regard to a method of preparing the sheet, that will be mentioned later according to the form of each material. Then the said sheet is subjected to a corrugating process under the conditions of a cell pitch width of 3.7 mm and a cell height of 2 mm, the resulting corrugated paper is made into a cylinder having a diameter of 38 mm at the opening and a length of 200 mm and the cylindrical product is used as a sample for the measurement. With regard to the measurement of the said sample, the sample is firstly dried under the conditions of 65° C. and an absolute humidity of 14 g/kg dry air. When it is confirmed that there is no change in the weight under the said condition, the drying treatment is finished and the weight at that time is defined as a dry weight (Wd1) After that, air of 27° C. and having an absolute humidity of 11 g/kg dry air is passed into the corrugated paper in a direction of the corrugated paper under the condition that face velocity at the pore cross section (38 mm diameter) of the product is 2 m/sec whereby moisture absorption is carried out. This moisture-absorbing operation is carried out for two minutes and the weight after the said two minutes is measured and defined as a moisture-absorbed weight (Ww1). The difference between the resulting moisture-absorbed weight (Ww1) and the dry weight (Wd1) is defined as a two-minute moisture-absorbed amount and is expressed in gram(s).

On the other hand, the moisture-desorbing rate is evaluated by a moisture desorbed amount during two minutes. Thus, a moisture-absorbing treatment is carried out under the conditions of at 27° C. and an absolute humidity of 11 g/kg dry air. When it is confirmed that there is no change in the weight under the said conditions, the moisture-absorbing treatment is finished and the weight at that time is defined as a moistened weight (Ww2) . After that, air of 65° C. and having an absolute humidity of 14 g/kg dry air is passed into the processed substance in a direction of the corrugated paper under the condition that face velocity at the pore cross section (38 mm diameter) of the substance is 2 m/sec whereby drying is carried out. This drying operation is carried out for two minutes and the weight after the said two minutes is measured and defined as a dry weight (Wd2). The difference between the resulting dry weight (Wd2) and the moistened weight (Ww2) is defined as a two-minute moisture-desorbed amount and is expressed in gram(s). In both cases of moisture-absorbing and desorbing rates, the more the two-minute moisture-absorbing and desorbing amounts, the higher the property.

Average particle size of the particles is measured as follows. Thus, a particle size distribution measuring device of a laser diffraction type (SALD 2000 manufactured by Shimadzu) is used, the result using water as a dispersing medium is expressed by volume and its medium diameter is adopted as an average particle size.

In the case of amount of carboxyl group of a potassium salt type, the polymer to be measured is subjected to a wet decomposition, amount of potassium contained therein is determined by an atomic absorption method and the amount of carboxyl group of a potassium type is calculated from the above result. With regard to the case of other alkaline metal type, amount of each metal is determined by means of an atomic absorption method and the amount of carboxyl group for each salt type is calculated.

Total amount of carboxyl group in the polymer is measured as follows. Thus, the polymer to be measured is dispersed in water and, after adjusting the pH to 2.0 with 1N hydrochloric acid, it is dried and weighed. Then the said adjusted sample is dispersed in water again, a titration is carried out using 0.1N aqueous solution of NaOH and, from the resulting titration curve, amount of carboxyl group by weight of the polymer of an H type (i.e., amount of carboxyl group of an H type) is calculated.

Example 1

Amberlite IRC 76 (a weakly acidic cation-exchange resin manufactured by Rohm & Haas) was made into a potassium type using a 1N aqueous solution of potassium hydroxide. Then the said resin was pulverized into fine particles of 10 μm or smaller using "Dyno-Mill" of Glen Mills Inc. Amount of carboxyl group of a potassium type in the resulting fine particles was 7.1 meq/g while the equilibrium moisture-absorbing ratio was 48%. To 100 parts of the fine particles of the moisture-absorbing and desorbing polymer were added 50 parts of a vinyl acetate emulsion containing 55% solid as a binder to prepare a liquid for application. The said liquid was applied to a paper (of a weight of 40 g/m$^2$) to make the carried amount of the said polymer 50 g/m$^2$ followed by drying. After drying, the resulting paper containing the moisture-absorbing and desorbing polymer particles was subjected to a corrugating treatment and the two-minute moisture-absorbing and desorbing rates were measured. The result is shown in Table 1 together with other evaluated items.

TABLE 1

| | Example | Comparative Examples | | | |
|---|---|---|---|---|---|
| | 1 | 1 | 2 | 3 | 4 |
| Amount of carboxyl group in H type (meq/g) | 10.2 | 10.2 | 10.2 | 10.2 | 10.2 |
| Type of salt | K | Li | Na | Rb | Cs |
| Amount of carboxyl group in salt type (meq/g) | 7.1 | 9.5 | 8.0 | 4.9 | 4.0 |
| Average particle size (μm) | 3 | 3 | 3 | 4 | 3 |
| Equilibrium moisture-absorbed ratio (%) | 53 | 51 | 62 | 43 | 35 |
| 2-Minute moisture-absorbed amount (g) | 0.86 | 0.052 | 0.57 | 0.69 | 0.55 |

TABLE 1-continued

| | Example | Comparative Examples | | | |
|---|---|---|---|---|---|
| | 1 | 1 | 2 | 3 | 4 |
| 2-Minute moisture-desorbed amount (g) | 1.08 | 0.070 | 0.69 | 0.83 | 0.71 |

Comparative Examples 1–4

An ion exchanging was carried out by the same method as in Example 1 for the ion other than potassium (Li, Na, Rb and Cs) using the corresponding hydroxide to prepare the resin in the corresponding salt type and, after pulverization, application and corrugation, moisture-absorbing and desorbing amounts within two minutes were measured. The result is shown in Table 1. Each of them was called Comparative Examples 1-4, respectively.

When Example 1 was compared with Comparative Examples 1-4, a Na type was best in terms of equilibrium moisture-absorbing ratio and was as high as 1.17-fold of potassium salt type which was the second best one and the ratios were in the order of Na>K=Li>Rb>Cs. On the other hand, in terms of the two-minute moisture-absorbing amount, the potassium type of the present invention was best and was confirmed to be as high as 1.25-fold of Rb salt type which was the second best one. In terms of moisture-desorbing rates, the order was as same as that in the case of moisture-absorbing rates and a potassium salt type was again confirmed to be best in the moisture-desorbing rate. Thus, it was proved that the moisture-absorbing and desorbing polymer of the present invention was very good in the moisture-absorbing and desorbing rates within a very short period of time.

Example 2

An acrylonitrile type polymer (10 parts) consisting of 90% by weight of acrylonitrile and 10% by weight of methyl acrylate was dissolved in 90 parts of 48% aqueous solution of sodium thiocyanate, the resulting polymer solution was impregnated into and adhered to a polypropylene nonwoven fabric to such an extent that the amount as a polymer solid was 30 g /m$^2$, and the fabric was dipped in water (20° C.) which was a non-solvent to coagulate whereupon a sheet product was prepared. The resulting sheet was well washed with water, then 50 parts of 60% by weight of hydrazine and 850 parts of water were added to 100 parts of the acrylonitrile type polymer carried on the sheet, a hydrazine treatment was carried out at 90° C. for 3 hours to introduce cross-links thereinto, then 100 parts potassium hydroxide were added thereto and a reaction was carried out at 120° C. for 5 hours to hydrolyze the remaining nitrile group whereupon a sheet carrying the moisture-absorbing and desorbing polymer having carboxyl group of a potassium type was prepared. The resulting sheet contained 49 g/m$^2$ of the moisture-absorbing and desorbing polymer and its characteristics such as equilibrium moisture-absorbing ratio are as shown in Table 2. The said sheet was subjected to a corrugating treatment under the already-mentioned condition and the two-minutes moisture-absorbing and desorbing rates were measured. Result of the measurement is shown in Table 2 as well. In the resulting moisture-absorbing and desorbing polymer in sheet, amount of carboxyl group of a potassium type is small and, therefore, both equilibrium moisture-absorbing ratio and two-minute moisture-absorbing and desorbing amounts were less than those in Example 1 although the resulting moisture-absorbing and desorbing rates were confirmed to be better than those of a sodium type of Comparative Example 2. Unlike Example 1, no binder (which was thought to suppress the moisture-absorbing and desorbing rates) was used in Example 2 and, probably because of that, there was a characteristic feature that, as compared with Example 1, decrease in the moisture-absorbing rate was not so significant as the decreasing ratio of the amount of carboxyl group of a potassium type.

TABLE 2

|  | Examples | | | Comparative Examples | |
| --- | --- | --- | --- | --- | --- |
|  | 2 | 3 | 4 | 5 | 6 |
| Amount of carboxyl group in H type (meq/g) | 6.2 | 7.4 | 7.5 | 0.96 | 12.8 |
| Type of salt | K | K | K | K | K |
| Amount of carboxyl group in salt type (meq/g) | 5.4 | 5.7 | 5.8 | 0.91 | 8.7 |
| Equilibrium moisture-absorbed ratio (%) | 41 | 44 | 49 | 11 | 25 |
| 2-Minute moisture-absorbed amount (g) | 0.76 | 0.82 | 0.95 | 0.008 | — |
| 2-Minute moisture-desorbed amount (g) | 0.92 | 1.02 | 1.19 | 0.009 | — |

Example 3

The same operation as in Example 2 was carried out except that a solution of acrylonitrile type polymer solution prepared in Example 2 was spun from a spinning nozzle having a pore diameter of 60 μm into a spinning bath where the bath temperature was −2° C and 15% aqueous solution of sodium thiocyanate was used as a non-solvent followed by elongating and washing with water to give fibrous acrylonitrile type polymer whereupon a fibrous moisture-absorbing and desorbing polymer having a fiber diameter of about 18 μm of the present invention was prepared. After that, 50 parts of the said fiber, 40 parts of pulp and 10 parts of vinylon fiber were mixed and made into paper to give paper which was a paper product of a weight of 100 g/m² containing a fibrous moisture-absorbing and desorbing polymer. This paper was corrugated under the already-mentioned condition and the two-minute moisture-absorbing and desorbing rates were measured. Result of the evaluation is shown in Table 2. It was confirmed that, even when the moisture-absorbing and desorbing polymer is fibrous, the moisture-absorbing and desorbing rates were better than in the case of the sodium salt type of Comparative Example 2. The two-minute moisture-absorbing and desorbing rates were nearly the same as good as those in Example 1 while, in the case of fibrous form, deformation of corrugated paper was noted probably due to expansion and shrinking of the fiber as a result of moisture-absorption and desorption.

Example 4

The same operation as in Example 3 was carried out except that spinning into a spinning bath of water of a bath temperature of +10° C. was conducted whereupon porous and fibrous moisture-absorbing and desorbing polymer having a fiber diameter of about 20 μm was prepared. Further, the same paper manufacture and corrugating operation as in Example 3 were carried out and the resulting product in a form of paper was subjected to a measurement of the two-minute moisture-absorbing and desorbing rates. Result of the evaluation is as shown in Table 2 and the best moisture-absorbing and desorbing rates were noted. Especially when compared with Example 3, it was confirmed that, in spite of the fact that the amount of carboxyl group in a potassium type is nearly the same, quicker moisture-absorbing and desorbing rates were able to be expressed due to porosity. Incidentally, specific surface area and average pore size of the said fiber were 19.5 m²/g and 0.065 μm, respectively.

Comparative Example 5

A water-soluble polymer (300 parts) consisting of methacrylic acid and sodium p-styrenesulfonate (70:30) and 30 parts of sodium sulfate were dissolved in 6595 parts of water and placed in a polymerization vessel equipped with a paddle-shaped stirrer. After that, 15 parts of 2,2'-azobis (2,4-dimethylvaleronitrile) were dissolved in a mixture of 2300 parts of methyl methacrylate, 250 parts of methacrylic acid and 500 parts of divinylbenzene, placed in a polymerization vessel and subjected to a suspension polymerization at 60° C. for 2 hours under a stirring condition of 300 rpm to give a cross-linked copolymer of methyl methacrylate/ methacrylic acid/divinylbenzene having an average particle size of 60 μm. Since the resulting polymer was a carboxylic acid type, it was adjusted to pH 12 using 0.1N aqueous solution of potassium hydroxide at room temperature to give a potassium type. The resulting particles were pulverized, applied and corrugated by the same manner as in Example 1 and the two-minute moisture-absorbing and desorbing rates were measured. The evaluated result is shown in Table 2 and, since the amount of carboxyl group of a potassium type was very little, equilibrium moisture-absorbing ratio was low and the two-minute moisture-absorbing and desorbing rates were extremely slow as well whereby the product is meaningless in practical use.

Comparative Example 6

A water-soluble polymer (300 parts) consisting of methacrylic acid and sodium p-styrenesulfonate (70:30) and 30 parts of sodium sulfate were dissolved in 6600 parts of water and placed in a polymerization vessel equipped with a paddle-shaped stirrer. After that, 15 parts of 2,2'-azobis (2,4-dimethylvaleronitrile) were dissolved in a mixture of 2900 parts of methyl acrylate and 150 parts of divinylbenzene, placed in a polymerization vessel and subjected to a suspension polymerization at 60° C. for 2 hours under a stirring condition of 300 rpm to give a cross-linked copolymer of methyl acrylate/divinylbenzene having an average particle size of 63 μm. The said polymer (100 parts) was dispersed in 900 parts of water, 100 parts of potassium hydroxide were added thereto and the mixture was made to react at 90° C. for 2 hours to hydrolyze a methyl ester moiety of methyl acrylate whereupon polymer particles having 8.7 meq/g of carboxyl group of a potassium type were prepared. Average particle size of the said polymer particles was swollen by the hydrolysis showing the size of as big as 230 μm and they were almost in a state of gel. When the product was dried, it showed tackiness and was hard to handle. Pulverization was then tried but, in a dry process, it became too hard while, in a wet process, swelling was significant and pulverization was impossible. Therefore, it was not possible to measure the moisture-absorbing and desorbing rates during two minutes. The equilibrium moisture-absorbing ratio was also low like in the highly water-absorbing resins. They are probably due to the fact that amount of carboxyl group of a potassium type became too much whereby the above problems were resulted.

According to the present invention, organic polymer containing a specific polar group is utilized whereby it is now possible to offer a polymer which has good moisture-absorbing and desorbing properties and is able to express the said moisture-absorbing and desorbing properties within a short period of time. Thus, it is the remarkable advantage of the present invention to be able to offer a polymer having good moisture-absorbing and desorbing rates which have not been available up to now.

As a result of utilization of the function of the moisture-absorbing and desorbing polymer of the present invention, the polymer can be applied to various fields such as fiber, processed fiber, sheet, paper, nonwoven fabric, film, binder, paint, adhesive, sensor, resin, electricity and electronics.

What is claimed is:

1. A moisture-absorbing and desorbing polymer which is an organic molecular substance comprising 1.0 –8.0 meq/g of carboxyl group of a potassium salt type and having a crosslinked structure, said organic molecular substance being obtained by polymerizing (1) a vinyl monomer having a carboxyl group on a side chain, (2) a vinyl monomer having a functional group which can be modified to a carboxyl group, said functional group being selected from the group consisting of a cyano group, an ester group, an amide group, an aldehyde group and an acid anhydride on a side chain, or (3) a mixture of said vinyl monomers (1) and (2) and the moiety derived from said vinyl monomer (2) in the resulting polymer is modified to a carboxyl group.

2. The moisture-absorbing and desorbing polymer according to claim 1, wherein said polymer is in any form selected from the group consisting of fiber, particles and sheet.

3. A composition comprising the moisture-absorbing and desorbing polymer according to claim 1.

4. A composition comprising the moisture-absorbing and desorbing polymer according to claim 2.

5. The moisture-absorbing and desorbing polymer according to claim 1, which has a two minutes moisture absorbing ability of an amount not less than 0.76 g and a two minutes moisture desorbing ability of an amount not less than 0.92 g.

6. The moisture-absorbing and desorbing polymer according to claim 2, which has a two minutes moisture absorbing ability of an amount not less than 0.76 g and a two minutes moisture desorption ability of an amount not less than 0.92 g.

* * * * *